(12) United States Patent
Thompson et al.

(10) Patent No.: US 9,395,280 B2
(45) Date of Patent: *Jul. 19, 2016

(54) GAS-LINE PROBE ADAPTER FOR CONNECTING VACUUM JACKETING

(71) Applicant: Mustang Sampling LLC, Ravenswood, WV (US)

(72) Inventors: Kenneth O. Thompson, Ravenswood, WV (US); Claude A. Rolston, St. Marys, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 184 days.

This patent is subject to a terminal disclaimer.

(21) Appl. No.: 14/180,641

(22) Filed: Feb. 14, 2014

(65) Prior Publication Data

US 2014/0260695 A1    Sep. 18, 2014

Related U.S. Application Data

(60) Provisional application No. 61/783,484, filed on Mar. 14, 2013.

(51) Int. Cl.
*G01N 1/22* (2006.01)
*G01N 1/20* (2006.01)

(52) U.S. Cl.
CPC ........... *G01N 1/2035* (2013.01); *Y10T 29/4973* (2015.01)

(58) Field of Classification Search
CPC . G01N 1/10; G01N 1/2035; G01N 2001/205; Y10T 29/4973; F17C 7/04; F17C 9/02
See application file for complete search history.

(56) References Cited

U.S. PATENT DOCUMENTS

| 4,015,479 A * | 4/1977 | Apple ................. G01N 1/2258 73/863.24 |
|---|---|---|
| 5,531,130 A | 7/1996 | Welker |
| 5,597,009 A | 1/1997 | Scherrer et al. |
| 7,162,933 B2 | 1/2007 | Thompson et al. |
| 7,484,404 B2 | 2/2009 | Thompson et al. |

(Continued)

FOREIGN PATENT DOCUMENTS

| WO | 2012/080619 A1 | 6/2012 | |
| WO | WO2012/080619 * | 6/2012 | ............... F17C 7/04 |

OTHER PUBLICATIONS

International Application No. PCT/US2014/026262, Notification of Transmittal of the International Search Report and the Written Opinion of the International Searching Authority, or the Declaration, dated, Jul. 18, 2014.

(Continued)

*Primary Examiner* — Peter Macchiarolo
*Assistant Examiner* — Natalie Huls
(74) *Attorney, Agent, or Firm* — Cahn & Samuels, LLP

(57) ABSTRACT

A vacuum jacketed gas line adaptor with a flange cover for an existing pipeline sample take-off probe encasing a sample line and hermetically sealed to a vacuum valve housing having an sealable access port and containing a vented bleed valve and a block valve, fluidly connected to the sample line and a length of vacuum jacketed tubing sealing connected to the valve housing and in vacuum communication therewith, where the vacuum jacketed tubing surrounds the sample line to provide thermal isolation from the ambient for the sample line to a sample vaporizer.

7 Claims, 3 Drawing Sheets

(56) References Cited

U.S. PATENT DOCUMENTS

| | | | |
|---|---|---|---|
| 8,056,399 | B2 | 11/2011 | Thompson et al. |
| 9,164,016 | B2 * | 10/2015 | Barere ................... F17C 7/04 |
| 2010/0012201 | A1 * | 1/2010 | Welker ................ F16K 15/028 |
| | | | 137/535 |
| 2011/0192174 | A1 | 8/2011 | Robidou et al. |
| 2013/0192339 | A1 | 8/2013 | Kriel et al. |
| 2014/0144254 | A1 * | 5/2014 | Thompson ........... G01N 1/2247 |
| | | | 73/863.11 |

OTHER PUBLICATIONS

Opta-Periph, "LNG Autosampler for Automatic Filling of Laboratory Cylinders, Model ISOSAMPLE 8100 Technical Quotation", dated Jan. 16, 2013.

Opta-Periph, "LNG Probe & Vaporizer BTU Sampling System LNG Quality Tracker Contaminants Sampling System, Model ISOPROBE 8100 Technical Quotation", dated Jan. 30, 2013.

Opta-Periph, "Sample Take-Off Probe & Vaporizer for LNG".

* cited by examiner

GAS-LINE PROBE ADAPTER FOR CONNECTING VACUUM JACKETING

FIELD OF INVENTION

This invention relates to an adapter for a LNG sample line probe. The adapter is connectable without the need to shut down a transmission pipeline and provides a structure that permits greater geometric design flexibility and extendability of a gas line connection between the sample probe and an associated sample conditioning vaporizer unit while preserving thermal isolation via vacuum jacketing.

BACKGROUND

A known issue associated with existing LNG Sample Vaporizer take-off probe assemblies is the limitation typically encountered in placement of an associated sample conditioning vaporizer assembly. Due to design limitations, such probes as for example, that described in the take off assembly embodied in US Pub App 2013263680 published Oct. 10, 2013 from Opta-Periph (See FIG. 1), are "deadheaded" into an LNG pipeline. That is, the probe P which projects into a pipeline interior, is welded to a flange F and bolted to the pipeline flange (not shown). The probe flange forms the base of an evacuable housing disposed directly above with a vacuum fitting and cryogenic control valve entry port project laterally. This arrangement limits design flexibility in spacing, geometry, and equipment selection. Moreover, replacement or maintenance of an existing probe and sample gas takeoff line requires the underlying LNG transmission pipeline to be shut down and purged. Additionally, the spacing of the vaporizer from the associated sample analyzer is restricted to a short distance. The limitation on the length between the take off and analyzer is attributed to the effort to minimize adverse thermal effects, e.g., dew point dropout, fractionation, or the like during transit of the extracted fluid to the associated sample conditioning vaporizer. This requirement limits system design by having to closely space a vaporizer and associated analyzer close to an LNG gas line probe.

SUMMARY OF INVENTION

It is an object of the present invention to overcome the aforementioned problems associated with conventional structures of the prior art.

It is another object of the present invention to provide a novel sample probe takeoff adapter particularly suited for liquid natural gas (LNG) transmission facilities.

Another object of the present invention is to provide an expedient to overcome recognized problems with existing sample take-off probe/sample conditioning equipment.

A further object of the present invention is to provide greater flexibility in the design and installation of sample takeoff equipment and more particularly, to minimize issues of equipment placement due to space constraints when involved with fractionable cryogenic fluids and particularly, LNG.

Still another of the present invention is to solve the problem of vaporizer positioning and associated design constraints typically encountered in the use of a deadhead probe sample take off.

It is another object of the present invention to provide a novel sample probe takeoff adapter permitting retrofitting installation without the need to disrupt LNG transport/transmission.

Yet another object of the invention is to provide a convenient, integrated substitute structure for an existing segment between a take-off probe and an associated gas sample vaporizer unit disposed downstream from the probe.

These and other objects are satisfied by a vacuum jacketed probe adapter for connecting to a cryogenic liquid pipeline probe including a sample take-off line, a cryogenic valve and a vacuum port connection, said adapter comprising a flange member of a select length and first cross-section dimension adapted to overlie and enclose the probe and hermetically seal the probe from an ambient environment, a first length of hollow vacuum tubing with a first end and a second end, having a cross-sectional dimension corresponding to that of the flange member to be hermetically sealable thereto at said first end and projecting from said flange member hermetically sealable to the flange, a valve housing defining a chamber and at least a first, second and third entry ports spaced from the probe, said valve housing being hermetically sealed to the second end of the first length of hollow vacuum tubing at said first entry port, said second entry port having an sealable door for access to the interior of the valve housing, said housing enclosing a first cryogenic venting bleed valve and a second cryogenic blocking valve, said cryogenic bleed and block valves being accessible through said second entry port, a sample takeoff line for transmitting a cryogenic liquid sample from the probe, extending centrally through the first length of hollow vacuum tubing, said take off line connectable to the probe and projecting into said valve housing, said sample take off line being connected to said first cryogenic venting bleed valve and then exiting the valve housing from said a second cryogenic blocking valve through said third entry port, a second length of hollow vacuum tubing with a first end and a second end, hermetically connected to said third entry port at said first end of said second length of hollow vacuum tubing, said sample take off line being disposed within and extending centrally through said second length of hollow vacuum tubing, and a connector in said take-off line formed proximate to the second end of said second length of hollow vacuum tubing to feed the content of the take-off sample into a vaporizer cabinet.

Other objects are satisfied by a vacuum jacketed probe adapter for retrofitting to an existing pipeline sample collecting probe, comprising an elongated vacuum sealable cover member, a sample line, a vacuum valve housing having an sealable access port and containing a vented bleed valve and a block valve, said valves being fluidly connected to the sample line and a length of vacuum jacketed tubing sealing connected to the valve housing and in vacuum communication therewith, said vacuum jacketed tubing surrounding said sample line for a select length up to ten meters and having an exit opening adapted for connection to a sample vaporizer.

Still other objects are satisfied by the method of for retrofitting an existing in-line sample take-off probe with an elongated vacuum sealable cover member, a sample line, a valve housing having an sealable access port, a vacuum port, and containing a vented bleed valve and a block valve, said valves being fluidly connected to the sample line, said valve housing being connected to and in vacuum communication with a length of vacuum jacketed tubing sealing connected to the valve housing and in vacuum communication therewith, said vacuum jacketed tubing surrounding said sample line for a select length up to ten meters and having an exit opening adapted for connection to a sample vaporizer vacuum jacketing, comprising the steps of: affixing the elongated cover member to the existing take-off probe; connecting the sample line to the take-off probe and the block and bleed valves; securing the elongated cover member to the valve housing;

securing the vacuum jacketed tubing to the valve housing and the sample vaporizer; and creating a thermally insulating vacuum around the sample line in the valve housing and vacuum jacketed tubing by evacuating through the vacuum port The invention herein is an adapter particularly suited for retrofitting vacuum jacketed tubing to a cryogenic style probe such as that depicted in FIG. 1. The invention relates generally to an adapter capable of providing remote placement from a probe that can be either for original or retrofit applications. The invention facilitates connecting vacuum jacketed tubing to an existing gas-line/input probe structures. The vacuum jacketed tubing of the invention is employed to maintain thermal stasis of cryogenic liquid from an LNG line takeoff probe sample point to a sample conditioning system/analyzer system that can be located up to ten meters from the vaporizer. The invention maintains cryogenic sample temperatures and provides a double block-and-bleed valve arrangement to provide increased reliability and operational isolation from the point of sample.

The adapter of the present invention is designed to assure a vacuum tight connection is maintained in respect to the probe and vacuum jacketed tubing. In the context of gas sampling line application, such vacuum is maintained between the sample probe piping and adapter in order to minimize heat transfer.

The inner tube carries the cryogenic liquid sample from the probe to a vaporizer unit while the outer tube maintains a constant and effective vacuum around and for the entire length of the liquid carrying inner tube. By this construction, the tube length can reach preferably, about seven, but up to ten meters to connect the probe with an associated vaporizer unit while preserving the inner tube liquid sample at cryogenic temperatures to prevent pre-vaporization.

Upon establishment of tight connections between a probe connection point and a section of vacuum jacketed tubing, a vacuum is then established internal to the adapter which serves to minimize heat transfer in either direction. Accordingly, the internal associated process tubing is then maintained at substantially the same temperature as the cryogenic liquid natural gas (LNG) and analysis harmful pre-vaporization is prevented.

For definitional purposes and as used herein "connected" includes physical, whether direct or indirect, affixed or adjustably mounted, as for example, the sanitary flange coupling is connected to the cryogenic take off probe vacuum valve, the vacuum jacketed tubing is hermetically connected to the associated vaporizer unit and the vacuum port is connectable to a vacuum line. Thus, unless specified, connected is intended to embrace any operationally functional connection.

As used herein "pipeline" means a pipeline in the conventional sense as well as any large receptacle for transmission of cryogenic liquid natural gas such as ships, railcars or trucks.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Figure 1:
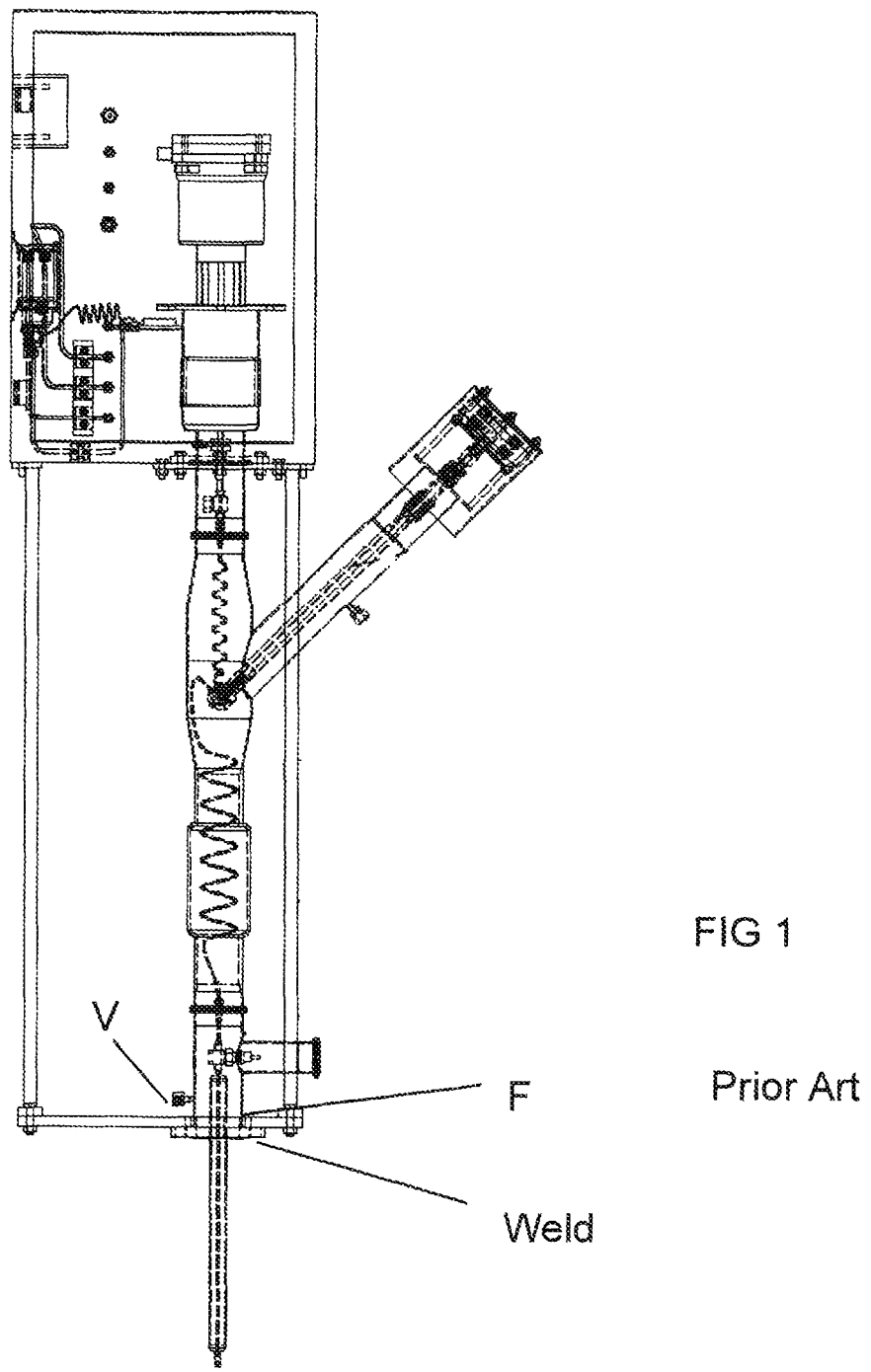
FIG. 1 is a depiction of a prior art device for sampling and vaporizing liquid natural gas.
Figure 2:
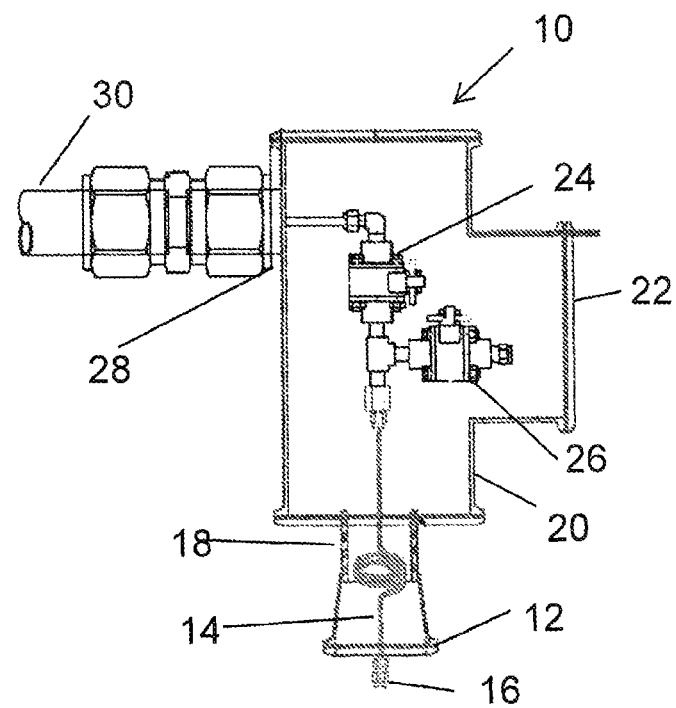
FIG. 2 is a side elevational view of an adapter according to one embodiment of the invention.
Figure 3:
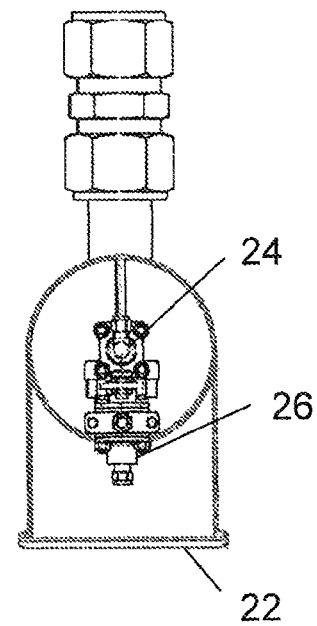
FIG. 3 is a plan view of the embodiment of FIG. 2
Figure 4:
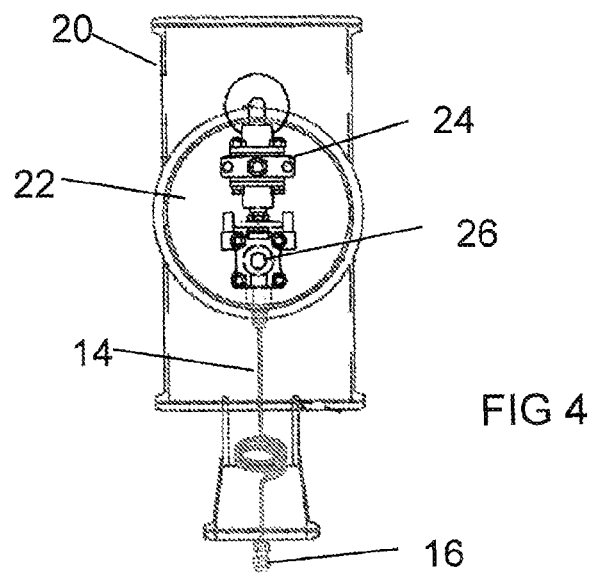
FIG. 4 is a front elevational view of the embodiment of FIG. 2.

In the simplest of explanations, and referring to the prior art represented by FIG. 1, the present invention is intended to provide a vacuum jacketed adapter structure 10 that connects with and complements an existing pipeline sample take-off probe to overcome the restrictions resulting from typical deadheading of sample probe/vaporizer units and control of gas take off sampling without the need to shut down and purge the pipeline source. The lower portion of the vacuum jacketed adapter structure 10 comprises a sanitary flange 12 housing a sample line 14 stainless steel tubing (typically 0.25 in diameter) with a compression coupling 16 for attachment to an existing cryogenic valve disposed substantially at the top of the probe. The compression coupling 16 is hermetically sealed to a select length of hollow tubing 18 (preferably 2.0 in. diameter). The tubing 18 is hollow to permit generally complete evacuation thereof when the sample take-off unit is in operation. At its upper end, the tubing 18 is compression coupled or welded to an opening in the base of a valve housing 20.

The illustrated valve housing 20 is in the form of a large hollow T comprising A3 piping with the leg of the T projecting horizontally. The valve housing 20 incorporates three main access points, the first comprising the sample gas line feed-through established with tubing 18, the second formed in the horizontal leg to provide access to the enclosed gas-line valves—the block valve 24 and the bleed valve 26—and the third comprising the gas line exit through the compression fitting 28. In alignment, preferably the bleed valve 26 is located in the sample gas line before the block valve 24 to allow for isolation and draining of the gas sample line independent of shutting down the entire probe/pipeline unit.

The valve housing 20 provides a secure enclosure for the block and bleed isolation valves 24 and 26 in addition to providing hermetic sealing for an internal vacuum to provide thermal insulation against the undesired temperature rise attributable to exposure of the sampled liquid in the gas line. Access to the enclosed valves is facilitated by a movable, hermetically sealable, access door 22. The door provides a commodious access portal, preferably large enough to accommodate the hand of a field worker/installer and any associated tools used in for manipulation of the block and bleed valves to minimize time and effort required for isolation function, maintenance, or troubleshooting.

Referring to the relative positioning of the sample gas line 14 in the context of the present invention, it enters the housing 20 through the welded base flange connected to the vacuum tubing length 18 extending co-linearly along the central axis thereof so as to maintain maximum separation from the perimetric walls. The sample line 14 projects into the evacuated housing interior to a coupling for venting/bleed valve 26 followed by blocking valve 24 from which the gas line elbows to exit the housing through a hermetically sealed vacuum tubing compression fitting 28. From there, the gas line extends along the central axis of the connected vacuum jacketed tubing 30 (generally having about a 2 inch diameter) which is of a selected length to reach an entry port in an associated vaporizer cabinet (not illustrated).

System operational and maintenance flexibility may be enhanced by incorporating a vacuum port in housing 20 to supplement a vacuum port in the existing probe structure. For additional safety, access door 22 may also incorporate a vacuum plug for pressure relief and a vacuum status indicator if the internal pressure goes positive. Such an indicator may be electrical or mechanical, e.g., a pressure relief plug with an outwardly deformable diaphragm serving as a signal indicating trouble. Alternatively, an electronic sensor may be employed for signal generation of status to a remote control station.

Figure 5:
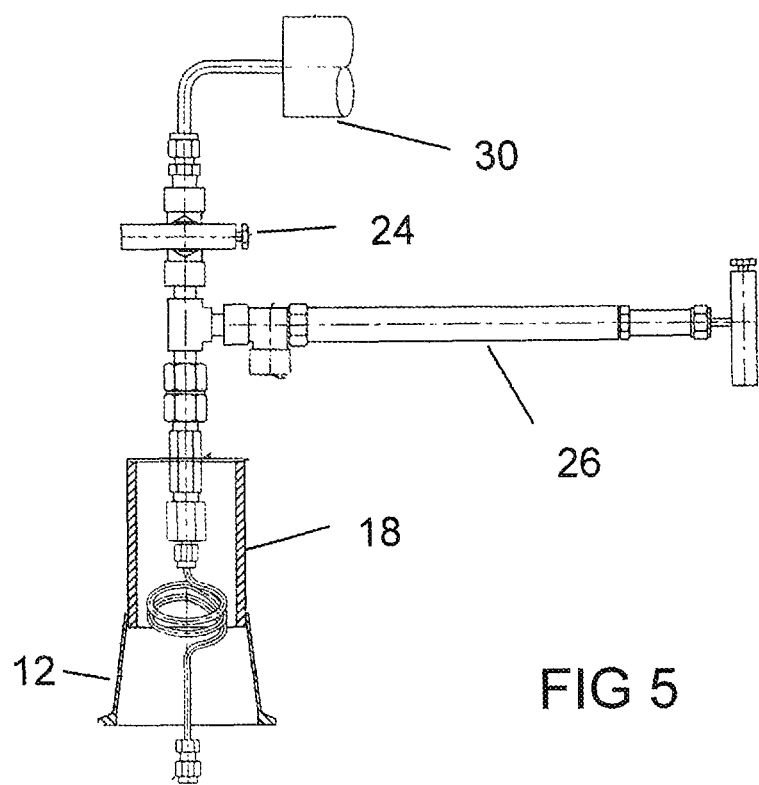
FIG. 5 is a partial schematic representative of a double block and bleed valve system to allow for isolation of the takeoff probe from the downstream vaporizer.

FIG. 5 schematically represents the internal components of the adapter according to the invention which, as illustrated, incorporate internal sample line isolation, cryogenic block valve 24 and vented bleed valve 26. The block and bleed valve arrangement is intended to supplement the existing take-off probe cryogenic valve by providing complementary/redundant sample gas line control. Thus, the present invention is characterizable as enhancing sample take-off safety and reliability by using vacuum jacketed tubing for thermal isolation of the sample gas line from the ambient and providing a double block and bleed facility between the probe and the existing adapter housing structure.

Referring now to installation of the instant invention, particularly, in the context of retrofitting to an existing dead-headed system, it contemplates first closing the cryogenic block valve at the upper end of the probe, removal of the existing vaporizer and intermediate tubing section. Utilization of the existing blocking valve dispenses with the need to shut down and bleed off the existing pipeline. Once the old equipment has been removed, sample gas line is connected to the existing isolation valve. Upon establishing the connection with the probe valve, the adapter is then slid back down to establish a connection with the probe housing which is tightened to provide hermetic sealing to allow the vacuum tubing 18, housing 20 and vacuum jacketed tubing 30 housing to be established. Upon securing all of the clamps and connections, a conventional vacuum pump (typically located near the vaporizer) and in vacuum communication with the tubing and adapter housing, is activated to establish an thermally insulating vacuum about the sample gas line contained in the adaptor structure.

The invention has been disclosed in the forgoing specification. It is understood by those skilled in the art that many modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

We claim:

1. A vacuum jacketed probe adapter for connecting to a cryogenic liquid pipeline probe including a sample take-off line, a cryogenic valve and a vacuum port connection, said adapter comprising:
  a) a flange member of a select length and first cross-section dimension adapted to overlie and enclose the cryogenic liquid pipeline probe and hermetically seal the cryogenic liquid pipeline probe from an ambient environment;
  b) a first length of hollow vacuum tubing with a first end and a second end, having a cross-sectional dimension corresponding to that of the flange member to be hermetically sealable thereto at said first end and projecting from said flange member hermetically sealable to the flange;
  c) a valve housing defining a chamber and at least a first, second and third entry ports spaced from the cryogenic liquid pipeline probe, said valve housing being hermetically sealed to the second end of the first length of hollow vacuum tubing at said first entry port, said second entry port having a sealable door for access to the interior of the valve housing, said valve housing enclosing a first cryogenic venting bleed valve and a second cryogenic blocking valve, said cryogenic bleed and blocking valves being accessible through said second entry port;
  d) a sample take-off line for transmitting a cryogenic liquid sample from the cryogenic liquid pipeline probe, extending centrally through the first length of hollow vacuum tubing, said take-off line connectable to the cryogenic liquid pipeline probe and projecting into said valve housing, said sample take-off line being connected to said first cryogenic venting bleed valve and then exiting the valve housing from said a second cryogenic blocking valve through said third entry port;
  e) a second length of hollow vacuum tubing with a first end and a second end, hermetically connected to said third entry port at said first end of said second length of hollow vacuum tubing, said sample take-off line being disposed within and extending centrally through said second length of hollow vacuum tubing; and
  f) a connector in said take-off line formed proximate to the second end of said second length of hollow vacuum tubing to feed the content of the take-off sample into a vaporizer cabinet.

2. The vacuum jacketed probe adapter of claim 1 where the flange member and the first length of hollow vacuum tubing are cylindrical.

3. The vacuum jacketed probe adapter of claim 2 where the valve housing is T-shaped with a horizontally projecting leg where the leg includes the second entry port.

4. The vacuum jacketed probe adapter of claim 3 where the second entry port includes a removable access door.

5. The vacuum jacketed probe adapter of claim 4 where third entry port is disposed oppositely of the second entry port and the sample line elbows above the cryogenic blocking valve to exit the valve housing chamber through the third entry port.

6. The vacuum jacketed probe adapter of claim 3 where the valve housing includes a vacuum port.

7. The vacuum jacketed probe adapter of claim 6 where the first length of hollow vacuum tubing, the valve housing chamber and the second length of hollow vacuum tubing are evacuable by the vacuum port.

* * * * *